United States Patent [19]

Weber et al.

[11] Patent Number: 5,948,688
[45] Date of Patent: Sep. 7, 1999

[54] METHOD OF DETERMINING MONOMERIC DRUG CONTENT

[75] Inventors: Patricia C. Weber, Yardley, Pa.; Ashit K. Ganguly, Upper Montclair, N.J.; Eric W. Kaler, Newark, Del.

[73] Assignee: Schering Corporation, Kenilworth, N.J.

[21] Appl. No.: 08/923,684

[22] Filed: Sep. 4, 1997

Related U.S. Application Data

[62] Continuation-in-part of application No. 08/708,513, Sep. 5, 1996, which is a continuation-in-part of application No. 08/211,700, filed as application No. PCT/US92/08565, Oct. 14, 1992, Pat. No. 5,624,914, which is a continuation-in-part of application No. 07/777,864, Oct. 16, 1991, abandoned.

[51] Int. Cl.⁶ .................................................. G01N 21/47
[52] U.S. Cl. .............................. 436/71; 436/94; 436/164; 356/336
[58] Field of Search ................................. 436/71, 94, 164; 356/336, 337

[56] References Cited

U.S. PATENT DOCUMENTS

| | | | |
|---|---|---|---|
| 4,164,558 | 8/1979 | Von Schulthess et al. | 424/12 |
| 4,521,521 | 6/1985 | Abbott et al. | 436/517 |
| 5,284,149 | 2/1994 | Dhadwal et al. | 128/665 |
| 5,624,914 | 4/1997 | Patel et al. . | |
| 5,763,600 | 6/1998 | Ganguly et al. | 536/123 |
| 5,776,912 | 7/1998 | Patel et al. | 514/54 |

FOREIGN PATENT DOCUMENTS

WO8702366  4/1987  WIPO .

OTHER PUBLICATIONS

H. Madani and E.W. Kaler, "Measurement of Polydisperse Colloidal Suspensions with Quasielastic Light Scattering," Part. Part. Syst. Charact. 8 (1991), pp. 259–266.

Ganguly, A. K., et al, Kirk–Othmer, Encyclopedia of Chemical Technology, (1978), 3rd Ed., vol. 2, 986–990.

Girijavallabhan, V.M., Ganguly, A.K., Kirk–Othmer, Encyclopedia of Chemical Technology (1992) 4th Ed. vol. 3, 259–266.

*Primary Examiner*—Jeffrey Snay
*Attorney, Agent, or Firm*—Joseph T. Majka

[57] ABSTRACT

A method of analyzing pharmaceutically useful suspensions of lipophilic oligosaccharide antibiotics by QLS is disclosed.

6 Claims, No Drawings

METHOD OF DETERMINING MONOMERIC DRUG CONTENT

The present application is a continuation-in-part of U.S. application Ser. No. 08/708,513 filed Sep. 5, 1996, which is a continuation-in-part of U.S. application Ser. No. 08/211,700 filed Apr. 12, 1994, now U.S. Pat. No. 5,624,914 which is the United States national application corresponding to International Application No. PCT/US92/08565, filed Oct. 14, 1992 and designating the United States, which PCT application is in turn a continuation-in-part of U.S. application Ser. No. 07/777,864 filed Oct. 16, 1991, now abandoned, the benefit of which applications are claimed pursuant to the provisions of 35 U.S.C. 120, 363 and 365(C).

BACKGROUND OF THE INVENTION

Quasielastic light scattering ("QLS"), also known as photon correlation spectroscopy, is a technique which, in certain instances, can be used to determine various physical characteristics of a particulate suspended in a liquid and/or the nature of the suspension itself. See Madani and Kaler (Part. Syst. Charact., Vol. 8, pp. 259–266, (1991)), Berne and Pecora ("Dynamic Light Scattering," John Wiley, New York, 1976) and D. H. Everett, "Basic Principles of Colloid Science," Royal Society of Chemistry, London 1988). QLS is based on determining the velocity distribution or particle movement by measuring dynamic fluctuations of intensity of scattered light. The disperse particles of macromolecules are suspended in a liquid medium undergo Browning motion which causes fluctuations of the local concentration of the particles. This results in local inhomogeneities of the refractive index which in turn results in fluctuations of intensity of the scattered light. The linewidth of the light scattered spectrum (defined as the half-width at half-maximum) is proportional to the diffusion coefficient of the particles.

However, this technique cannot be applied to all suspensions. Certain suspensions, because of the concentration of the particles, the size and/or size distribution of the particles, the type of particles, the possibility of interparticulate interactions, the type of media and the overall light absorption properties of the system, are not suitable for analysis using this technique.

U.S. Pat. No. 5,624,914 to Patel et al., the text of which is incorporated by reference, discloses certain lipophilic oligosaccharide antibiotics in specific physical forms, as well as formulations which establish or maintain the drug in those forms. A reliable and accurate method of confirming the form(s) of those active drugs in suspension would be highly desirable. A technique which could also confirm the effects on the suspension of various suspending agents in various proportions would also be useful. QLS has not previously been used for characterizing antibiotic-containing suspensions and in particular, suspensions of lipophilic oligosaccharide antibiotics and salts thereof.

SUMMARY OF THE INVENTION

It has been discovered that certain suspensions of lipophilic oligosaccharide antibiotics are susceptible to analysis by QLS. It has also been discovered that QLS can be used to evaluate the effect on the physical condition of a lipophilic oligosaccharide antibiotic in suspension, as well as suspensions resulting from certain changes in the composition or proportions of the suspending liquid.

Therefore in accordance with one aspect of the present invention there is provided a method of evaluating a lipophilic oligosaccharide antibiotic-containing suspension. A suspension including a lipophilic oligosaccharide antibiotic and a carrier liquid are provided and a laser beam is passed therethrough. The scattering of the light from the laser beam is then measured by QLS. Finally, the hydrodynamic radius of the lipophilic oligosaccharide antibiotic can be determined. In addition, the contribution of a particular form of the lipophilic oligosaccharide antibiotic to the total intensity of the linewidth distribution function can be determined. The former information can be used to evaluate the form(s) of the drug in the suspension, i.e., classes of particles (monomeric, dimeric, trimeric, multimeric). The latter information can be equated with the amount of particles of a specific hydrodynamic radius found in the suspension. Thus, the size, the form and the content of a class of particles can be determined for one or all of the particles in suspension.

Similarly, the effects of changing the suspending or carrier liquid on the state of the lipophilic oligosaccharide antibiotic can be evaluated by analysis of changes in the sizes and/or content of various forms of the drug.

In particular, it has been discovered that a formulation including a lipophilic oligosaccharide antibiotic suspended in a medium of water along with at least one other material selected from the group consisting of a base, a cyclodextrin, a surfactant and a saccharide can be analyzed by QLS.

DETAILED DESCRIPTION OF THE PREFERRED EMBODIMENTS

Lipophilic oligosaccharide antibiotics, also referred to as "drugs", in accordance with the present invention, include members of the orthosomycin family and contain at least one acidic phenolic hydrogen and two orthoester linkages associated with carbohydrate residues. These include, without limitation, everninomicins, curamycins, avilamycins, and flambamycins. Particularly preferred are the antibiotic compounds of the everninomicin class and in particular, antibiotics of the following formula I

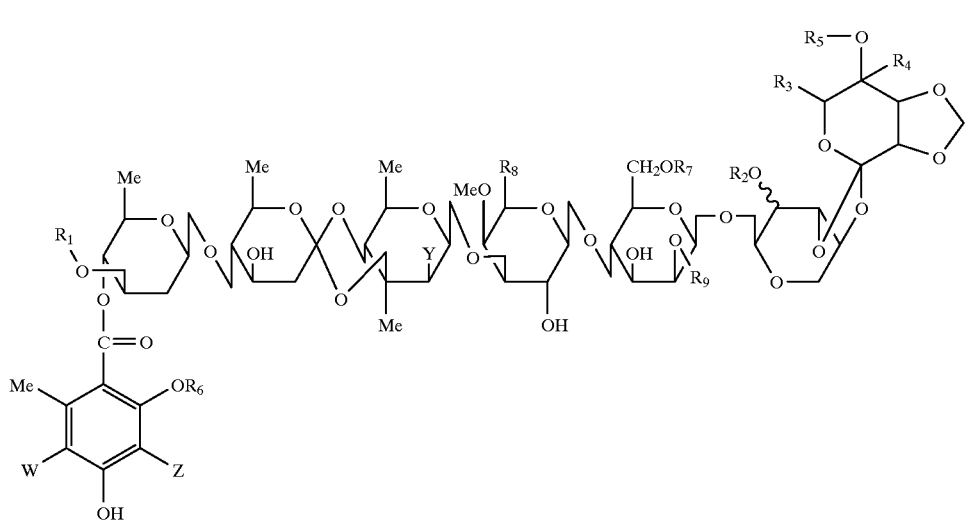

wherein

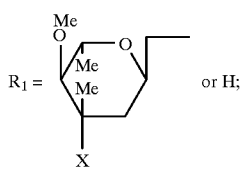

X is one of $NO_2$, NO, $NH_2$, $NHCOCH_3$, NHOH, $NH(C_2H_5)$, $N(C_2H_5)_2$, OH or H;

$R_2$ is one of $CH_3$, $COCH(CH_3)_2$, $COCH_3$, $CO(CH_2)_3CH_3COCH_2CH_3$ or H;

$R_3$ is one of $CH_3$ or H;

$R_4$ is one of $COCH_3$, $CH(OCH_3)(CH_3)$, $CH(OH)CH_3$, CHO, or H;

$R_5$ is one of

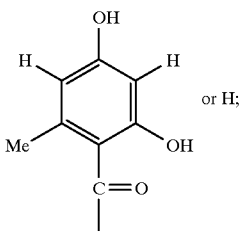

$R_6$ is $CH_3$ or H;
$R_7$ is $CH_3$ or H;
$R_8$ is $CH_3$, $CH_2OH$ or H;
$R_9$ is $CH_3$ or H;
Y is OH, $CH_3$, or H;
W is Cl or H; and
Z is Cl or H.

Of these, the following lipophilic oligosaccharide antibiotic class is more preferred:

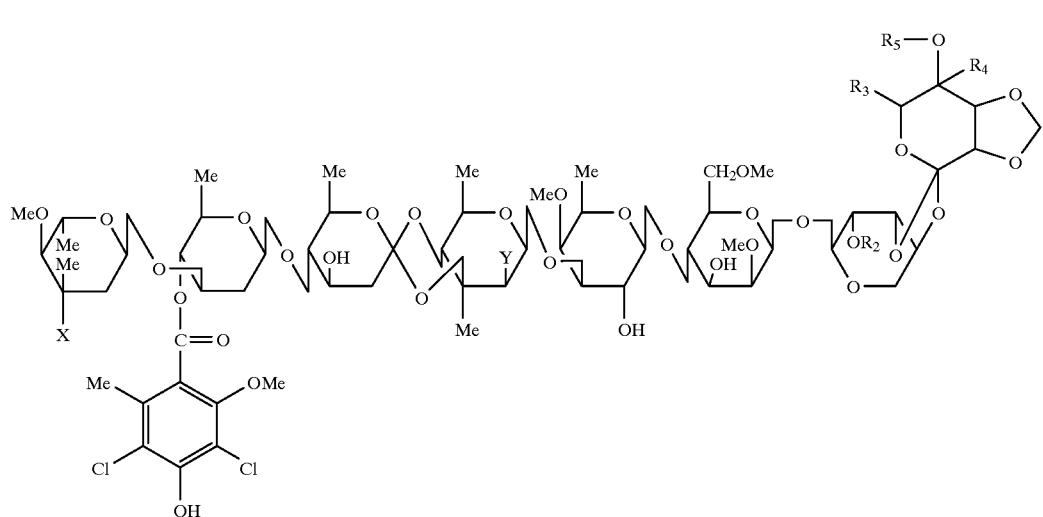
wherein X is one of $NO_2$, NO, NHOH, $NH_2$, $NHCOCH_3$, $NHC_2H_5$, $N(C_2H_5)_2$, OH or H
Y is OH or H
$R_2$ is H or $CH_3$
$R_3$ is H
$R_4$ is H or $CH(OCH_3)(CH_3)$ and
$R_5$ is H or
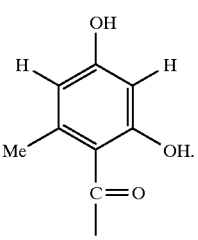
Of these, the following lipophilic oligosaccharide antibiotic of formula III is most preferred:
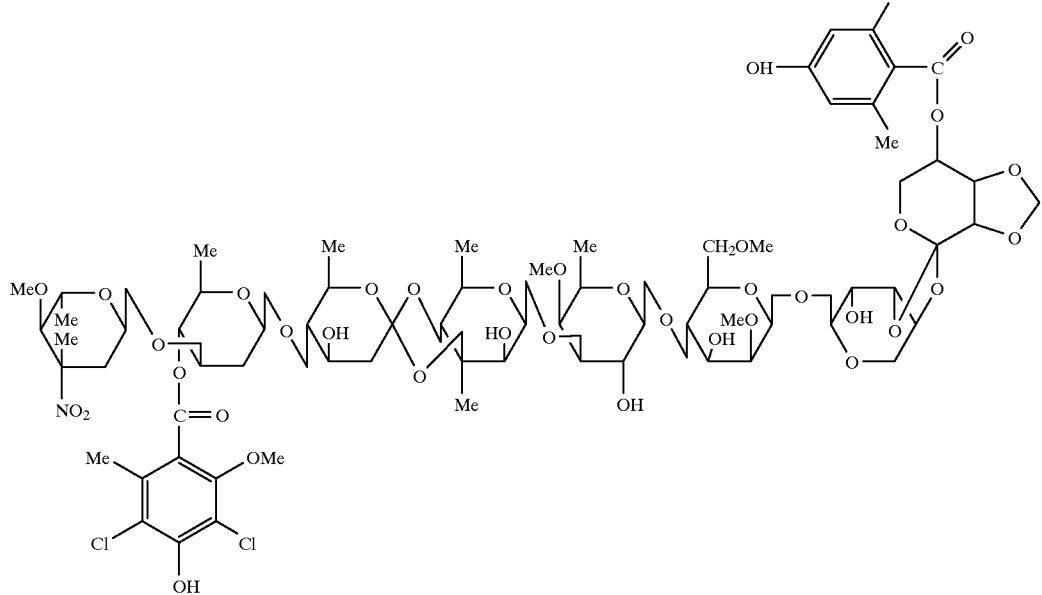

Any carrier liquid suitable for suspending the lipophilic oligosaccharide antibiotic is acceptable so long as it is neither so opaque nor so absorbent that it prevents the use of QLS. These include, without limitation: water, alcohol, oils and polyols. As the present invention relates to drug formulations, all of these carrier or suspending liquids must be pharmaceutically acceptable and safe. Sterilized water is preferred. It is also noteworthy that the formulations tested herein are not accurately called solutions, but are more properly considered colloidal suspensions; although, they may have properties of solutions such as being visually clear.

Additional agents may also be present to alter the solubility and/or suspension characteristics of the liquid. These can include any of the material described in U.S. Pat. No. 5,624,914, already incorporated by reference. These include, without limitation: co-solvents, bases, solubilizing agents, surfactants, excipients and the like.

Bases include substances which form pharmaceutically acceptable salts of the lipophilic oligosaccharide antibiotics used and include both organic and inorganic bases. Normal, alkyl, cyclic and aromatic amines are useful as organic bases with the referred base being N-methyl glucamine (NMG).

Solubilizing agents, include cyclodextrins and in particular hydroxy propyl-α, β-orγ-cyclodextrins are preferred.

Surfactants include dimethylsulfoxide, glycerol and sorbitan mono-9-octadecenoate poly(oxy-1,2ethanediyl) derivatives such as polysorbate 80 (Tween 80), as well as dextrans.

Excipients include, for example saccharides such as glucose, mannitol, dextrose, sorbitol, and xylitol, salts such as sodium chloride, nitrates such as potassium nitrate, and buffers such as phosphate buffers.

In the practice of the invention, a suspension containing a lipophilic oligosaccharide antibiotic is prepared. This can be accomplished in any way known to the skilled formulator. For the sake of illustration only, a hydroxy propyl, -β-cyclodextrin (HPβCD) containing 7.4 hydroxpropyl groups per molecule can be added to an aqueous solution of NMG and the lipophilic oligosaccharide antibiotic of Formula III. To this solution can be added granular mannitol, USP grade and Polysorbate-80 (Tween-80) NF. The relative proportions of these ingredients may be varied so long as a stable suspension is found. The properties of the suspension can be determined at this point or the so-formed suspension can be filtered and freeze-dried. In some instances, where storage stability may be an issue, it may be desirable to perform QLS before freeze-drying and also at some later date following the re-introduction of the formulation into suspension, If freeze-dried, the freeze-dried composition can be stored in vials in a moisture-free environment. For preparation of a pharmaceutical composition suitable of i.v. administration from the freeze-dried composition, a predetermined amount of a carrier such as sterile water is added.

Following addition of the sterile water, the composition can be analyzed by QLS using a variety of techniques such as those described in Madani and Kaler (Part. Syst. Charact., Vol. 8, pp. 259–266, (1991)), Berne and Pecora ("Dynamic Light Scattering," John Wiley, New York, 1976) and/or D. H. Everett, "Basic Principles of Colloid Science," Royal Society of Chemistry, London 1988). This can be accomplished using a variety of commercially available spectrometers such as the Brookhaven Model BI-200SM goniometer using a Model BI-9000AT correlator and a Lexel 300mW Ar laser (488 nm wavelength). Samples are placed in 12 mL disposable glass analysis tubes and equilibrated for 10 min. in the instrument at 25° C.

Analyses of the data collected can indicate that the lipophilic oligosaccharide antibiotic or salt thereof exists as particles of one or more sizes and the hydrodynamic radius (R) of the various classes of particles can be determined in Angstroms (Å) by solving for the following equation:

$$R = kT/6\pi\mu D,$$

where R is the hydrodynamic radius, k is Boltzman's Constant, T is temperature, $\pi$ is pi, $\mu$ is viscosity and D is the diffusion coefficient. By determining the size of a particular particle, it is possible to also determine something about the aggregative form of that material. For example, a lipophilic oligosaccharide can exist in suspension in a multiplicity of different sizes equating to monomeric, dimeric and various multimeric forms. By determining the relative sizes of various particles, one can understand the full nature of the suspension and all of the particulate forms of the drug.

In addition, the contribution of a particular particle to the total intensity of the linewidth distribution function, $G(\Gamma)$ can be used to evaluate the relative proportion of a particular sized particle. This presumes that $$G(\Gamma) = M^2(r)P(q)S(q)$$

where $G(\Gamma)$ is the linewidth distribution function, $M(r)$ is the mass distribution of the particles of size r, $P(q)$ is the particle form factor and $S(q)$ is the static structure factor. $G(\Gamma)$ is derived from quasielastic light scattering procedures which measure the intensity autocorrelation function, $g^{(2)}(\tau)$, wherein $$g^{(2)}(\tau) = A(1+\beta|g^{(1)}(\tau)|^2)$$

where $g^{(2)}(\tau)$ is the intensity autocorrelation function, A is the background scattered intensity, $\beta$ is the signal-to-noise ratio, and $g^{(1)}(\tau)$ is the electric field autocorrelation function. The measured intensity autocorrelation function, $g^{(2)}(\tau)$, is related to the linewidth distribution function, $G(\Gamma)$, by the following formula:

$$g^{(1)}(\tau) = \int_{\infty}^{\infty} G(\Gamma)\exp(-\Gamma\tau)d\Gamma$$

where $g^{(1)}(\tau)$ is the electric field autocorrelation function. The decay constant, $\Gamma$, equals $Dq^2$ where D is the diffusion coefficient and q is the magnitude of the scattering vector where $q = 4\pi n\lambda \sin(\Theta/2)]$ where $\pi$ is pi, n is the refractive index of the medium, $\lambda$ is the wavelength of light in vacuum and $\Theta$ is the scattering angle.

If the same procedure is repeated with a different drug content, a suspending liquid including the same components in different proportions, or a different suspending formulation, then the effects thereof on the physical characteristics of the lipophilic oligosaccharide antibiotic and/or the suspension can be determined. This is accomplished by comparing the results of the two formulations in terms of the presence or absence of certain sized particles as well as any changes in the relative proportion of the particles.

EXAMPLE 1

An aqueous solution containing 23.97 mg of N-methyl glucamine ("NMG") and 570.90 mg of 2-hydroxypropyl-β-cyclodextrin ("HPβCD") having 7.4 hydroxypropyl groups per molecule of HPβCD was prepared in 5 mL of water.

To this solution was added 100 mg of the compound of Formula III. After mild agitation, a homogeneous complex containing 20 mg per mL of the compound of Formula III was formed. The molar ratios of the three components were 1 mole of the compound of Formula III to 2 moles of "NMG" to 6 moles of HPβCD. The so-formed solution was filtered through a 0.45 μm membrane and freeze-dried and stored in a moisture-free environment. For preparation of a pharmaceutical composition, a pharmaceutically acceptable carrier such as water was added.

EXAMPLE 2

The procedure of Example 3A is followed except that 1750 mg of HPβCD containing 7.4 hydroxpropyl groups per molecule was added to an aqueous solution of 126 mg of NMG and 350 mg of the compound of Formula III. The molar ratios of the three components in the homogeneous solution so-formed were 1 mole of the compound of Formula III to 3 moles of NMG to 5 moles of HPβCD. To this solution were added 500 mg of granular mannitol, USP grade and 10 mg of Polysorbate-80 (Tween-80) NF. The weight percent of Tween-80 is 2.85% basis the compound of Formula III. The so-formed solution was filtered and freeze-dried.

The freeze-dried composition is stored in vials in a moisture-free environment. A pharmaceutical composition suitable of i.v. administration, was formed by adding 30 mL of sterile water to the vial. Following addition of the sterile water, the aqueous pharmaceutical composition was analyzed by PCS at 90° scattering angle, using a Brookhaven a Model BI-200SM goniometer with a Model BI-9000AT correlator and a Lexel 300 mW Ar laser (488 nm wavelength). The Analyses indicated that the aqueous pharmaceutical composition contained, inter alia, the lipophilic oligosaccharide antibiotic of Formula III thereof in a particle from having a hydrodynamic radius (R) of about 20 to 30 Angstroms (Å) or less.

This meant that the antibiotic of formula III was present in monomeric form. In addition, these particles of monomeric form contributed at least 35%, a substantial amount, of the total intensity of the linewidth distribution function. This means that about 80 to about 90 percent or greater of the drug by weight was present in this class of sized particles, in this system. The remaining drug was present in other forms, the size, number of molecules of drug aggregate (dimer, trimer, multimer), and relative proportion of which could all be determined in a similar manner.

We claim:

1. A method of evaluating a lipophilic oligosaccharide antibiotic containing suspension comprising the steps of:

providing a suspension including particles of a lipophilic oligosaccharide antibiotic and a carrier liquid;

passing a laser beam through said suspension;

measuring the scattering of the light from said laser beam as it passes through said suspension; and determining a characteristic of at least one of said suspended particles selected from the group consisting of the hydrodynamic radius of said particle and the proportion of said particles having a certain hydrodynamic radius within said suspension.

2. The method of claim 1 further comprising the step of preparing a suspension including particles of a lipophilic oligosaccharide antibiotic suspended in a carrier liquid of water and at least one other material selected from the group consisting of a base, a cyclodextrin, a surfactant and a saccharide, prior to said providing step.

3. A method of evaluating a lipophilic oligosaccharide antibiotic containing suspension comprising the steps of:

providing a suspension including particles of a lipophilic oligosaccharide antibiotic of formula I, II or III and a carrier liquid;

passing a laser beam through said suspension;

measuring the scattering of the light from said laser beam as it passes through said suspension; and determining a characteristic of at least one of said suspended particles selected from the group consisting of the hydrodynamic radius of said particle and the proportion of said particles having a certain hydrodynamic radius within said suspension.

4. The method of claim 3 further comprising the step of preparing a suspension including particles of a lipophilic oligosaccharide antibiotic suspended in a carrier liquid of water and at least one other material selected from the group consisting of a base, a cyclodextrin, a surfactant and a saccharide, prior to said providing step.

5. A method of evaluating a lipophilic oligosaccharide antibiotic containing suspension comprising the steps of:

providing a suspension including particles of a lipophilic oligosaccharide antibiotic of formula I and a carrier liquid;

passing a laser beam through said suspension;

measuring the scattering of the light from said laser beam as it passes through said suspension; and determining a characteristic of at least one of said suspended particles selected from the group consisting of the hydrodynamic radius of said particle and the proportion of said particles having a certain hydrodynamic radius within said suspension.

6. The method of claim 5 further comprising the step of preparing a suspension including particles of a lipophilic oligosaccharide antibiotic suspended in a carrier liquid of water and at least one other material selected from the group consisting of a base, a cyclodextrin, a surfactant and a saccharide, prior to said providing step.

* * * * *